(12) United States Patent
Thiel et al.

(10) Patent No.: US 7,259,279 B2
(45) Date of Patent: Aug. 21, 2007

(54) PROCESS FOR PREPARING ALDEHYDES

(75) Inventors: Dietmar Thiel, Oberhausen (DE); Carl Dieter Frohning, Wesel (DE)

(73) Assignee: Oxea GmbH, Oberhausen (DE)

( * ) Notice: Subject to any disclaimer, the term of this patent is extended or adjusted under 35 U.S.C. 154(b) by 137 days.

(21) Appl. No.: 11/274,079

(22) Filed: Nov. 15, 2005

(65) Prior Publication Data
US 2006/0161023 A1    Jul. 20, 2006

(30) Foreign Application Priority Data
Nov. 19, 2004 (DE) .................. 10 2004 055 832

(51) Int. Cl.
C07C 45/50 (2006.01)
G01N 31/00 (2006.01)
G06F 19/00 (2006.01)

(52) U.S. Cl. .................. 568/451; 702/22; 702/23; 702/26

(58) Field of Classification Search .................. None
See application file for complete search history.

(56) References Cited

FOREIGN PATENT DOCUMENTS

JP        EP0589463 A2 *  3/1994
SU         1527234 A1 *  12/1989

* cited by examiner

Primary Examiner—Sikarl A. Witherspoon
(74) Attorney, Agent, or Firm—Charles A. Muserlian

(57) ABSTRACT

Process for the hydroformylation of olefins by linkage of the input parameters prevailing in the hydroformylation reaction to the target parameters of a hydroformylation reaction, wherein the linkage is achieved by means of at least one synthetic neuronal network.

14 Claims, 2 Drawing Sheets

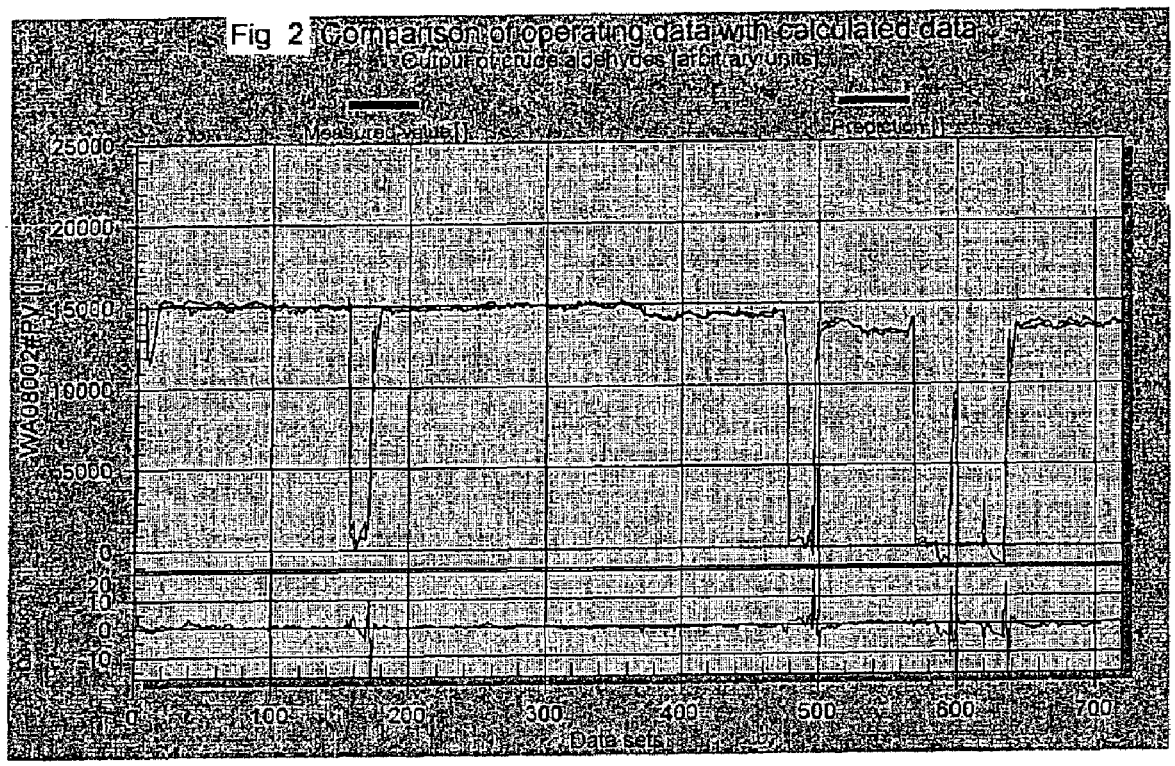

PROCESS FOR PREPARING ALDEHYDES

Figure 1:
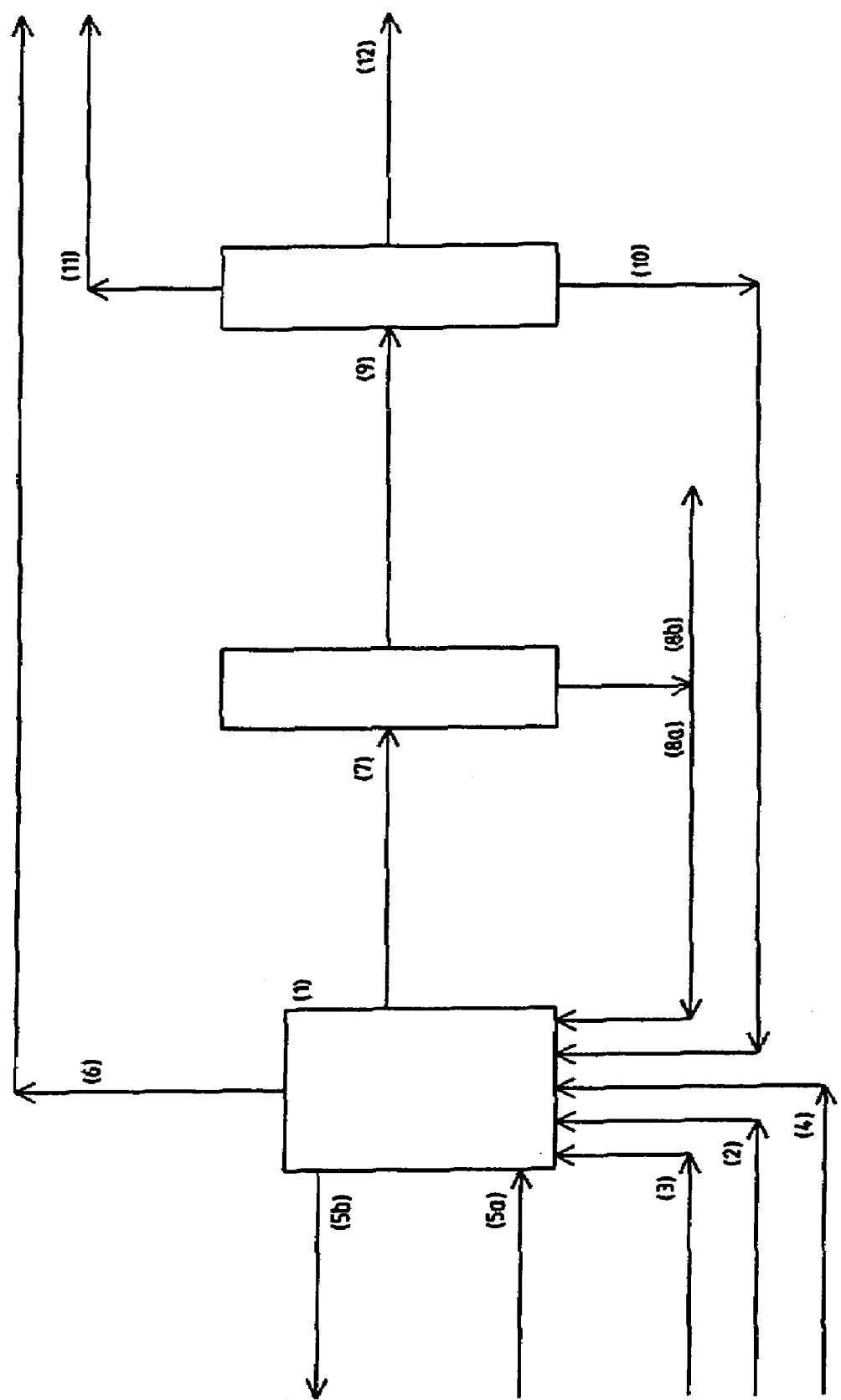

The present invention relates to a process for the hydroformylation of olefins using a synthetic neuronal network for monitoring and control.

The term hydroformylation refers to the reaction of olefins with hydrogen and carbon monoxide in the presence of transition metal catalysts to form aldehydes and alcohols which have one more carbon atom than the olefin used. Hydroformylation has considerable economic and industrial importance; at present, more than 6 million metric tons per annum of products are produced worldwide by hydroformylation processes. The aldehydes initially obtained are used as such or are valuable intermediates for the production of, for example, alcohols, carboxylic acids, esters or amines.

Hydroformylation is catalyzed by hydridometal carbonyls, preferably those of the metals of transition group VIII of the Periodic Table. Apart from cobalt, the classical catalyst metal, catalysts based on rhodium have been increasingly used as catalysts for some years. In contrast to cobalt, rhodium allows the reaction to be carried out at a lower pressure. In addition, when terminal olefins are used, straight-chain n-aldehydes are preferentially formed and isoaldehydes are formed to a subordinate extent. Finally, hydrogenation of the starting olefins to saturated hydrocarbons is significantly lower in the presence of rhodium catalysts than when cobalt catalysts are used.

The hydroformylation of olefinically unsaturated compounds is implemented industrially using rhodium carbonyl complexes comprising tertiary organic phosphines or phosphites as ligands as catalysts. In one process variant, the reaction is carried out in a homogeneous organic phase, i.e. the starting olefin, catalyst and reaction products are present together in solution. The reaction products are usually separated off from the mixture by distillation, more rarely by means of other processes such as extraction. The hydroformylation process carried out in a homogeneous phase can be in the form of a recycle gas process as described in U.S. Pat. No. 4,247,486 or in the form of a liquid recycle process as described in U.S. Pat. No. 4,148,830.

In a further process variant, an aqueous catalyst phase comprising rhodium carbonyl complexes and water-soluble organic phosphines is present. This embodiment is known, for example, from DE-B-26 27 354. Its particular advantage is the ease of separation of the organic reaction product and the aqueous catalyst phase, e.g. by phase separation. This separation is carried out under mild conditions and without use of thermal process steps and losses which can occur as a result of subsequent reactions of the aldehydes formed can be avoided. Furthermore, very high yields are achieved and when unbranched terminal olefins are used, very predominantly unbranched aldehydes are obtained. Owing to the presence of a liquid organic phase and an aqueous catalyst phase, this hydroformylation variant is also referred to as the heterogeneous or two-phase process. A tried and tested embodiment of this mode of operation is described, for example, in EP-B1-0 103 810.

Both the hydroformylation process carried out in a homogeneous phase and the heterogeneous hydroformylation process, which is also known as the Ruhrchemie/Rhone-Poulenc process, have become established in industrial practice and are comprehensively described in the literature, for example by C. D. Frohning, C. W. Kohlpaintner in B. Cornils/W. A. Herrmann, Applied Homogeneous Catalysis with Organometallic Compounds, Volume 1, 1st edition, pages 29-104, VCH Weinheim, 1996.

The processes operated industrially according to the variants mentioned have been continually improved over many years and therefore have a high degree of maturity which can be seen in the good utilization of materials and energy and the high operational reliability. Thus, in the hydroformylation of propylene, conversions of above 85%, based on propylene used, have been reported, with a ratio of n-butanal to isobutanal of above 90/10 being achieved at the same time.

FIG. 1 shows an in-principle outline of a hydroformylation process. Olefin (2) and synthesis gas (3), viz. a mixture of hydrogen and carbon monoxide, are fed into the cooled and stirred reactor (1). A further feed line (4) serves to supply further catalyst when this is required to maintain the catalyst concentration. The heat liberated in the hydroformylation is removed by means of a suitable cooling medium (5a and 5b). To limit the accumulation of inerts, an offgas stream (6) is taken off from the reactor (1). Unreacted starting materials, catalyst and reaction products are discharged from the reactor (1) and fractionated in a first downstream stage (7) from which the discharged catalyst (8a) is taken off and recirculated to the reactor (1). If required, part of the catalyst (8b) is discharged and passed to work-up and/or reactivation. In a further downstream stage (9), unreacted olefin and synthesis gas and also alkanes formed by hydrogenation of the olefin are separated off from the reaction mixture obtained after the catalyst has been separated off and are returned to the reactor as recycle gas (10), with a substream (11) having to be discharged as offgas to limit the accumulation of inerts in the reaction system. The reaction products (12) are passed to further processing.

Even from this greatly simplified scheme, it can be seen that control and monitoring of such a hydroformylation process is no trivial task. The measurement and regulation of the large number of streams and the associated residence times and also the setting and regulation of temperature, pressure and concentrations at many points in the process by themselves present considerable challenges. This is made even more difficult by a hydroformylation catalyst not having a constant activity over the operating time, but being changed in terms of its effectiveness by unavoidable ageing processes. The regulating system has to respond to these changes, for example by altering the respective operating temperature, the amounts of feed or the residence times, in order to keep the production level of the plant constant. Increasing the amount of rhodium present or the ligand concentration either continuously or stepwise is another task to be performed by the process control system, as is known, for example, from B. Cornils, E. Wiebus, Chem. Ing.-Techn. 1994, 66, 196; E. Wiebus, B. Cornils, Chemtech 1995, 25, 33.

A person skilled in the art will know from B. Cornils in J. Falbe (Ed.), New Syntheses with Carbon Monoxide, Springer-Verlag, Berlin 1980, 1st edition, that the reaction parameters for carrying out a hydroformylation reaction continuously cannot be chosen freely. As examples, the following general dependences may be mentioned:

(a) A high hydrogen partial pressure has a positive effect on the reaction rate. However, hydrogenation of the olefin to the alkane increases at the same time.

(b) A high carbon monoxide partial pressure has an adverse effect on the reaction rate and on the normal/iso ratio of the aldehydes formed and accelerates ligand degradation, but stabilizes rhodium carbonyl hydrides.

(c) A high reaction temperature has a positive effect on the reaction rate, but has an adverse effect on the stability of the catalyst.

(d) A large excess of ligand has a favourable effect on the normal/iso ratio of the aldehydes formed, but is disadvantageous in respect of the reaction rate.

Even these few examples make it clear that a large number of parameters have to be measured and regulated for the hydroformylation reaction to be carried out safely, technically successfully and economically successfully, with some of these parameters being dependent on one another and/or mutually influencing one another. When the hydroformylation of olefins is carried out industrially, it is therefore necessary to match many process parameters to one another and control them so that the desired values for desired target parameters, for example the aldehyde yield or the ratio of n-aldehyde to isoaldehyde, can be set reliably.

Although hydroformylation has been carried out on an industrial scale for many decades, it has to be surprising that no generally applicable mathematical model by means of which the reaction between olefin, carbon monoxide and hydrogen

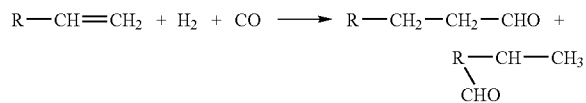

normal (n-)aldehyde iso(i-)aldehyde can be described quantitatively in terms of rate and extent as a function of the process parameters such as temperatures, partial pressures of olefin, hydrogen and carbon monoxide, concentration of catalyst and ligand has become known. Although examples of reaction rate equations are reported in the literature, for example S. S. Divekar, R. M. Deshpande, R. V. Chaudari, Catal. Lett. 1993, 21, 191, these were set up under idealized conditions and do not meet the requirements of a reliable industrial reaction procedure.

The modeling of the heterogeneous hydroformylation process in the presence of an aqueous catalyst solution, in which not only the chemical reaction but also the mass transfers between the gas phase, the liquid organic phase and the liquid aqueous catalyst phase which is likewise present and accordingly also the influence of the mixing of all three phases have to be taken into account, presents particular difficulties (K.-D. Wiese et al., Catalysis Today 79-80 (2003) 97-103).

The monitoring and control of a process for the hydroformylation of olefins has thus hitherto been carried out by means of empirical data acquired over long periods of operation.

Approaches for improving this state which is based on empirical data and is ultimately not fully satisfactory have become known.

Thus, EP-B1-589 463 relates to a method of controlling the normal/iso ratio of the aldehydes formed in a hydroformylation reaction between an olefin, hydrogen and carbon monoxide (CO) by controlling the CO partial pressure in the reaction system. According to the procedure claimed, the target value for the CO partial pressure is maintained in a reaction system by regulating either the flow rate of the synthesis gas (mixture of CO and hydrogen) fed into the system or the flow rate of the offgas leaving the system. The known method firstly describes measurement of the CO partial pressure, then the generation of control parameters which result from the difference between intended and actual value of the CO partial pressure, and finally the utilization of these control parameters for influencing the flow rate, with once again either the flow rate of the synthesis gas fed into the system or the flow rate of the offgas leaving the system being influenced. According to the known method, only one input parameter, namely the CO partial pressure, is linked to an output parameter, namely the normal/iso ratio of the aldehydes formed, with the magnitude of the CO partial pressure to be maintained being prescribed arbitrarily by the user. Further process parameters and target parameters are not taken into account.

In the case of SU 1 527 234, the amounts of synthesis gas and propylene introduced in the hydroformylation of propylene are regulated with the objective of keeping the amount of synthesis gas required low. A regulating system in which the respective volumes of feed gas and offgas are linked to one another is described. Further process parameters and target parameters are not taken into account.

It is accordingly an object of the invention to provide a hydroformylation process in which the process parameters to be taken into account, also referred to as input parameters, are linked quantitatively to the target parameters of the hydroformylation process, also referred to as output parameters, so that the prescribed values for the target parameters are achieved by setting of the associated process parameters. The hydroformylation process can be monitored and controlled in this way.

This object is achieved by a process for the hydroformylation of olefins by linkage of the input parameters prevailing in the hydroformylation reaction to the target parameters of a hydroformylation reaction, wherein the linkage is achieved by means of at least one synthetic neuronal network.

While the conventional approaches for improved monitoring and control of the hydroformylation reaction are based on measurement and regulation of a single critical parameter, or in any case very few such critical parameters, the use according to the invention of at least one synthetic neuronal network, hereinafter also referred to as SNN for short, makes possible a completely different, more comprehensive procedure.

The structure and function of an SNN allow a large number of process parameters to be processed as input parameters and a model which quantitatively describes the weighted influence of each parameter on the course and result of the process to be produced therefrom. As input parameters, it is possible to employ data which have already been obtained in the preceding course of the hydroformylation process. In this procedure, the SNN is trained and/or retrained.

However, in the preferred way of using the SNN, data from the ongoing hydroformylation process are fed into the SNN and the SNN is continually retrained as time goes on and automatically adapts and improves the quality of the internally generated model to the circumstances of the ongoing hydroformylation process. The independent learning capability of SNNs during the ongoing hydroformylation process is utilized in this way.

A further advantage of this procedure is that interventions into the hydroformylation reaction itself are not necessary, but instead the SNN utilizes only data which have previously been measured for monitoring and control of the hydroformylation process.

An important aspect of the present invention is that the SNN weights the input parameters, with absolute value and sign of the weights corresponding to the importance of the input parameter for the value of the target parameters.

A further important property of an SNN is that the algorithms necessary for linkage of the input parameter to the target parameters do not have to be known, but instead the SNN can itself derive the weights from the input data. An SNN can thus be trained, retrained or continually retrained, either on the basis of existing data or on the basis of data which are measured and fed into the SNN during the ongoing process. An SNN is thus capable of independently converting complex relationships between the input parameters or the process parameters and the output parameters or target parameters of the hydroformylation process into an algorithm which quantitatively describes these relationships. Once the algorithm has been derived, it then makes it possible to predict the target parameters from new data sets for the input parameters.

In carrying out hydroformylation reactions, the main dependences between the input parameters or reaction parameters and the target parameters such as olefin conversion, normal/iso ratio of the aldehydes formed, formation of alkanes and high boilers or catalyst deactivation are known in principle to those skilled in the art. However, the use according to the invention of an SNN for the first time enables the dependences between the individual process parameters and thus their mutual influences to be measured and quantified. Thus, the complex relationships of the hydroformylation reaction can for the first time be determined in their entirety and described quantitatively by means of a mathematical model.

SNNs are commercially available and can be linked to a freely available number of inputs, so that a corresponding large number of input parameters can be selected. These input parameters can in principle be chosen freely, but a person skilled in the art will advantageously choose only those input parameters whose importance for the result of the process, i.e. for the target parameters, is known or whose importance is to be specifically examined.

In the case of a hydroformylation process as shown in FIG. 1, it is possible, for example, to prescribe the following input parameters and target parameters or outputs.

Examples of input parameters or process parameters are: amount of olefin (2) introduced, amount of synthesis gas (3) introduced, temperature in the reactor (1), concentration of the catalyst in the reactor (1), concentration of ligands in the reactor (1), partial pressure of olefin in the reactor (1), partial pressure of hydrogen in the reactor (1), partial pressure of carbon monoxide in the reactor (1), volume of offgas (6) discharged from the reactor (1), amount of crude product (7) discharged from the reactor (1), volume of catalyst circulation (8), temperature of the catalyst circulation (8), volume of offgas (11) discharged from the gas removal (9), volume of recycle gas (10) recirculated to the reactor (1) from the gas removal (9).

Examples of target parameters or outputs are: mass of crude aldehydes, normal/iso ratio of the aldehydes, mass of alkane formed, mass of high boilers formed, olefin conversion.

The data required can be taken from any suitable source, for example from existing data sets. However, the input parameters are preferably taken from a process control system or some other process data logging system during the ongoing hydroformylation process and fed in a suitable way into the SNN, for example by means of an on-line connection to a data source. Temporary storage of the data on a databank server can offer advantages in the case of large quantities of data.

The SNN is provided with selected data at a point in time regarded as suitable and trained until the model produced quantitatively describes the relationships between input parameters and target parameters with the degree of accuracy required or sought.

The algorithm determined by the SNN subsequently serves as the basis for carrying out an optimization calculation using a conventional model, with the process parameters for this conventional model being restricted to the range determined by the input parameters for the SNN prevailing in the hydroformylation reaction. Commercially available SNNs frequently already contain an integrated function for carrying out optimization calculations using the algorithm generated by the SNN. It is likewise possible for the algorithm generated by the SNN to be passed to a conventional, commercially available model, for example a table calculation program, and carry out the optimization calculations in this programmed. The data obtained on the basis of the algorithm generated by the SNN can also be processed manually by the plant operator in order to optimize the process parameters.

The process parameters which have been optimized in this way are subsequently set in the industrial operation of the hydroformylation.

EXAMPLE 1

Example 1 demonstrates the application of an SNN to data from the process for the hydroformylation of propylene with the objective of obtaining an algorithm which quantitatively describes the target parameters as a function of a plurality of process parameters or input parameters.

A continuous hydroformylation of propylene by the heterogeneous two-phase process was carried out. The trisodium salt of tris(m-sulfophenyl)-phosphine (TPPTS) served as ligand for the rhodium catalyst dissolved in water. The concentration of rhodium in the aqueous catalyst solution was 255 ppm, and the molar ratio of ligand/rhodium was 87/1. Over a period of 15 days, the following average results were obtained:

| (1) | Temperature in the reactor [° C.] | 129.2 |
| (2) | Temperature of catalyst circuit [° C.] | 129.9 |
| (3) | Temperature of mixture of fresh gas + recycle gas at inlet of reactor [° C.] | 99.7 |
| (4) | Synthesis gas ($H_2$ + CO) fed in [standard $m^3$ per $m^3$ of catalyst and hour] | 96 |
| (5) | Propylene fed in [kg per $m^3$ of catalyst and hour] | 101.7 |
| (6) | Partial pressure of propylene in the reactor [MPa] | 2.0 |
| (7) | Output of crude aldehyde [kg per $m^3$ of catalyst and hour] | 144.3 |

[in (3), fresh gas is the mixture of synthesis gas and propylene fed into the hydroformylation reactor while recycle gas is the mixture of synthesis gas, propylene and alkanes which has been separated off from the process and recirculated to the reactor, reference numeral (10) in FIG. 1); in (4), standard m is standard cubic meters; at standard temperature $T_S$=273.15 K and standard pressure $P_S$=101 325 Pa]

A complete data set was determined every 30 minutes for positions (1) to (4) and for (6) and (7); a total of 722 data sets were collected in this way. Operation-related interruptions or malfunctions were included in these data sets, so that a typical course of the process was recorded. The 722 data sets were fed into an SNN (Neuromodel 2.0; from Atlantec, D 47877 Willich-Munchheide), with positions (1) to (4) and (6) being defined as input parameters, and position (7) being defined as output or target parameter. The training of the SNN by means of the 722 data sets led to an algorithm which made it possible to calculate the target parameter from the input parameters with a mean error of 1.1% of the value range of the target parameter. FIG. 2 shows the agreement between measured and calculated values for the target parameter, in particular with inclusion of operation-related interruptions to the process.

EXAMPLE 2

Example 2 shows the positive effect of the process parameters matched according to a prior calculation on the target parameter.

An optimization calculation for the amount of crude aldehydes produced was carried out by means of commercially available software using the algorithm obtained in Example 1. The function "Genetischer Optimierer®" integrated into the commercially available SNN Neuromodel 2.0 from Atlan-tec, D47877 Willich-Munchheide was employed for this purpose, with the process parameters being restricted to the range determined by the input parameters. The rhodium content of the aqueous catalyst solution and the molar ratio of TPPTS ligand/rhodium were not altered. The following results were obtained:

|     |     | Calculated | Best value |
| --- | --- | --- | --- |
| (1) | Temperature in the reactor [° C.] | 133.2 | 133.0 |
| (2) | Temperature of catalyst circuit [° C.] | 130.4 | 125.4 |
| (3) | Temperature of mixture of fresh gas + recycle gas at inlet of reactor [° C.] | 97.1 | 110.2 |
| (4) | Synthesis gas ($H_2$ + CO) fed in [standard $m^3$ per $m^3$ of catalyst and hour] | 134 | 108 |
| (5) | Propylene fed in [kg per $m^3$ of catalyst and hour] | 126.8 | 109.9 |
| (6) | Partial pressure of propylene in the reactor [MPa] | 2.03 | 2.02 |
| (7) | Output of crude aldehyde [kg per $m^3$ of catalyst and hour] | 206.9 | 172.2 |

The best value is the highest output of crude aldehydes which was obtained using the SNN over the period of operation considered as in Example 1. Setting of the previously calculated operating state gave the following result:

|     |     | Calculated | Obtained |
| --- | --- | --- | --- |
| (1) | Temperature in the reactor [° C.] | 133.2 | 133.0 |
| (2) | Temperature of catalyst circuit [° C.] | 130.4 | 129.4 |
| (3) | Temperature of mixture of fresh gas + recycle gas at inlet of reactor [° C.] | 97.1 | 98.3 |
| (4) | Synthesis gas ($H_2$ + CO) fed in [standard $m^3$ per $m^3$ of catalyst and hour] | 134 | 129 |
| (5) | Propylene fed in [kg per $m^3$ of catalyst and hour] | 126.8 | 122 |
| (6) | Partial pressure of propylene in the reactor [MPa] | 2.0 | 2.0 |
| (7) | Output of crude aldehyde [kg per $m^3$ of catalyst and hour] | 206.9 | 196 |

Comparison of the values calculated by means of the algorithm produced by the SNN with the values obtained in the hydroformylation process make it clear that careful matching of a plurality of previously calculated process parameters (input parameters) to one another enables the target parameter "output of crude aldehydes" to be lastingly influenced. Thus, matching of the process parameters (1)-(4) and (6) leads to a significant increase in the output of crude aldehydes from 144.3 kg per $m^3$ of catalyst and hour (Example 1) to 196 kg per $m^3$ of catalyst and hour (Example 2).

What we claim is:

1. A process for the hydroformylation of olefins by linkage of the input parameters prevailing in the hydroformylation reaction to the target parameters of a hydroformylation reaction, wherein the linkage is achieved by means of at least one synthetic neuronal network.

2. The process of claim 1, wherein the synthetic neuronal network is trained and/or retrained after the hydroformylation reaction by means of the input parameters prevailing in the hydroformylation reaction.

3. The process of claim 1, wherein the synthetic neuronal network is continually retrained during the hydroformylation reaction by means of the input parameters prevailing in the hydroformylation reaction.

4. The process of claim 3, wherein the continual retraining of the neuronal network is effected using the input parameters prevailing in the hydroformylation reaction which are taken from a process data logging system.

5. The process of claim 1, wherein the synthetic neuronal network weighs the input parameters according to their importance for the value of the target parameters.

6. The process of claim 1, wherein the linkage between input parameters and target parameters determined by means of a synthetic neuronal network is combined with a conventional model which carries out an optimization of the target parameter on the basis of the range determined by the input parameters.

7. The process of claim 1, wherein a synthetic neuronal network whose target parameter is the aldehyde output is used.

8. The process of claim 1, wherein a synthetic neuronal network whose target parameter is the ratio of n-aldehyde to isoaldehyde is used.

9. The process of claim 1, wherein a synthetic neuronal network whose target parameter is the amount of alkanes formed is used.

10. The process of claim 1, wherein a synthetic neuronal network whose target parameter is the amount of high boilers formed is used.

11. The process of claim 1, wherein a synthetic neuronal network whose target parameter is the olefin conversion is used.

12. The process of claim 1, wherein the reactor temperature, the catalyst circulation temperature, the temperature of a mixture of fresh gas and recycle gas, the amount of synthesis gas fed in and the olefin partial pressure in the reactor are used as input parameters prevailing in the hydroformylation reaction for the neuronal network.

13. The process of claim 1, wherein propylene, 1-butene, 2-butene or a mixture comprising 1-butene and 2-butene is used as olefin.

14. The process of claim 1, wherein the hydroformylation is carried out in a homogeneous organic reaction mixture or using an aqueous catalyst solution in a heterogeneous two-phase process.

* * * * *